United States Patent [19]

Cushman

[11] Patent Number: 4,997,269
[45] Date of Patent: Mar. 5, 1991

[54] SCHEINER-PRINCIPLE POCKET OPTOMETER FOR SELF EVALUATION AND BIO-FEEDBACK ACCOMMODATION TRAINING

[75] Inventor: William B. Cushman, Pensacola, Fla.

[73] Assignee: The United States of America as represented by the Secretary of the Navy, Washington, D.C.

[21] Appl. No.: 486,323

[22] Filed: Feb. 28, 1990

[51] Int. Cl.⁵ .............................................. A61B 3/00
[52] U.S. Cl. .................... 351/203; 351/211; 351/223; 351/239; 351/243
[58] Field of Search ............... 351/203, 211, 214, 215, 351/221, 223, 232, 234, 237, 239, 243, 246

[56] References Cited

U.S. PATENT DOCUMENTS

| | | | |
|---|---|---|---|
| 3,787,112 | 1/1974 | Lyons | 351/223 |
| 4,222,639 | 9/1980 | Sheedy | 351/243 |
| 4,943,151 | 7/1990 | Cushman | 351/203 |

*Primary Examiner*—Rodney B. Bovernick
*Attorney, Agent, or Firm*—Thomas E. McDonnell; George Jameson

[57] ABSTRACT

A method and optometer apparatus for measuring the accommodative state of an eye of a subject is disclosed. In a preferred embodiment, the optometer apparatus includes: a pinhole aperture plate having a center and a plurality of apertures in the pinhole aperture plate for viewing by the subject's eye; a positive lens disposed near the pinhole aperture plate and having an optical axis coincident with the center of the pinhole aperture plate; and scaled means inclined away from the positive lens for indicating to the subject the accommodative state of the subject's eye in diopters.

14 Claims, 1 Drawing Sheet

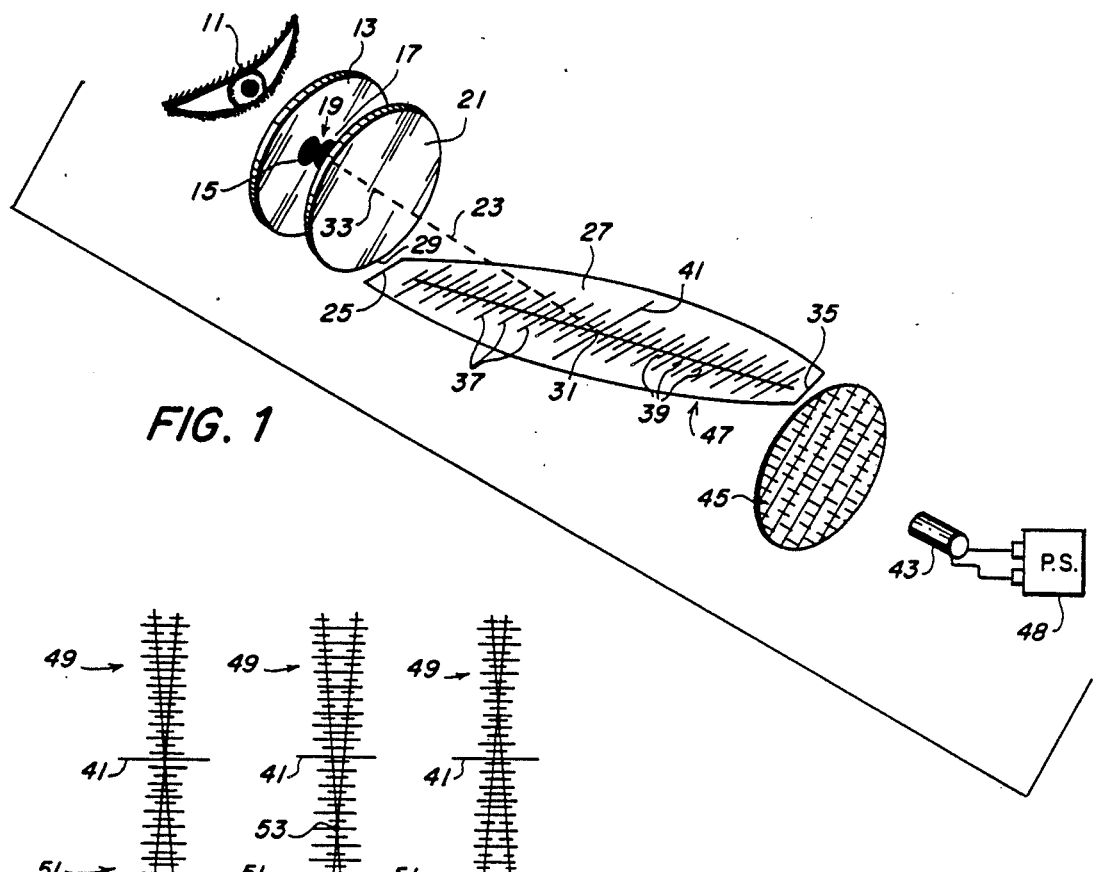
FIG. 1
FIG. 2A  FIG. 2B  FIG. 2C
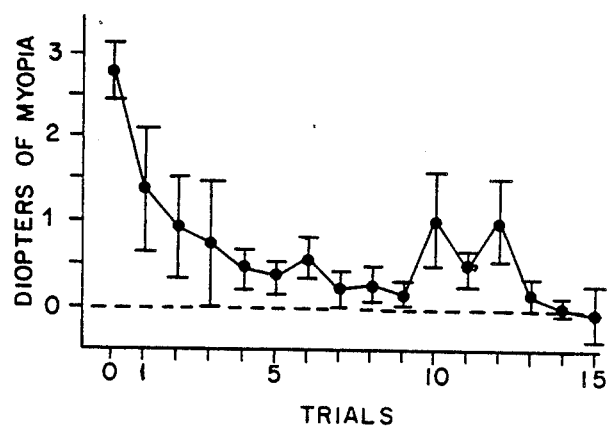
FIG. 3

ABSTRACT

SCHEINER-PRINCIPLE POCKET OPTOMETER FOR SELF EVALUATION AND BIO-FEEDBACK ACCOMMODATION TRAINING

CROSS-REFERENCE TO RELATED APPLICATION

This patent application is related to the co-pending U.S. patent application entitled "A Scheiner-Principle Vernier Optometer", Ser. No. 07/370,521, filed June 23, 1989, now U.S. Pat. No. 4,923,151, both of which applications having the same inventor and being commonly assigned to the Government of the United States.

BACKGROUND OF THE INVENTION

1. Field of the Invention

The present invention relates to optometers and particularly to a Scheiner-principle optometer apparatus, and method therefor, for measuring the resting state of accommodation, and for providing cognitive recognition of this accommodative state in order to facilitate bio-feedback training of that accommodative state.

2. Description of the Prior Art

The need for precise lens accommodation to bring visual targets into sharp focus on the retina is far more urgent at night when contrast is very low, than in bright daylight. Unfortunately, it is at precisely this time that many individuals become myopic and further reduce the quality of an already poor visual image. In many professions this phenomenon, sometimes called the "dark focus of accommodation", is of little consequence. However, for pilots flying at night it can mean the difference between life and death. A reliable screening instrument capable of measuring the refractive state of individuals in the dark could, therefore, provide useful preventive information.

In the case where this preventive information is cognitively available to the subject as he accommodates, a means of implementing a bio-feedback training paradigm exists. Bio-feedback training to correct night myopia is not new. In the publication of Randle, Robert J., "Volitional Control of Visual Accommodation", Conference Proceedings No. 82 on Adaptation and Acclimatization in Aerospace Medicine, Advisory Group for Aerospace Research and Development (AGARD), North Atlantic Treaty Organization, Garmisch-Partenkirchen, Germany, September 1970, successful bio-feedback accommodation training has been demonstrated, using a Stanford Research Institute dual Purkinje image eye-tracker with optometer attachment and auditory feedback. Other apparatuses, such as the apparatus for accommodation training disclosed in U.S. Pat. No. 4,660,945, could be used in a similar fashion. However, the apparatus involved in each of these examples is large, extremely expensive and requires a trained technician to operate.

OBJECTS OF THE INVENTION

Accordingly, it is an object of this invention to provide an improved optometer apparatus and method therefor.

Another object of this invention is to provide a Scheiner-principle optometer for self evaluation of accommodative state and bio-feedback training to remedy undesirable conditions such as dark or empty field myopia.

Another object of this invention is to provide a small, hand held, simple, economical, portable optometer for self evaluation and bio-feedback accommodation training.

A further object of this invention is to provide an improved optometer apparatus, and method therefor, which enables a subject to measure his accommodation state and to train himself to accommodate at infinity in the dark.

SUMMARY OF THE INVENTION

These and other objects of this invention are achieved by a method and optometer apparatus that includes: a pinhole aperture plate having a center and a plurality of apertures positioned in the pinhole aperture plate for viewing by the subject's eye; a positive lens disposed near the pinhole aperture plate and having an optical axis coincident with the center of the pinhole aperture plate; and scaled means inclined away from the positive lens for indicating to the subject the accommodative state of his eye in diopters.

BRIEF DESCRIPTION OF THE DRAWINGS

These and other objects, features and advantages of the invention, as well as the invention itself, will become better understood by reference to the following detailed description when considered in connection with the accompanying drawings wherein like reference numerals designate identical or corresponding parts throughout the several views, and wherein:

FIG. 1 illustrates a diagram of a preferred embodiment of the invention, showing the essential elements of the invention and their interrelationships with respect to one another;

FIGS. 2A, 2B and 2C show three views of the image seen by a user of the preferred embodiment of FIG. 1 during respective emmetropia, myopia and hyperopia conditions; and FIG. 3 illustrates a chart containing data samples collected from one subject while using the preferred embodiment of FIG. 1 for bio-feedback training to overcome night myopia.

DETAILED DESCRIPTION OF THE PREFERRED EMBODIMENT

Before proceeding with the Detailed Description, the terms "optometer", "Scheiner-principle optometer" and "dark focus of accomodation" are defined below to aid in the reader's understanding of the present invention.

Optometer—Any one of several objective or subjective devices for measuring the refractive state of the eye. (Synonym: opsimeter, optimeter, refractometer)

Scheiner-principle optometer—An optometer employing, as an operating principle, multiple pupillary apertures to produce a corresponding multiplicity of images when the image viewed is not in focus.

Dark focus of accommodation—A phenomenon, generally recognized as the "resting state" of the eye in the absence of sufficient stimulation to activate focusing mechanisms. This situation usually occurs in the dark and, thus, it is called the "dark focus of accommodation". This "resting state" in the dark is typically myopic, so a synonym for the phenomenon is "night myopia". A related phenomenon occurs when light is being received by the eye but there is no detail (as, for example, when flying in a cloud). This related phenomenon is called "empty field myopia".

Referring now to the drawings, FIG. 1 shows a preferred embodiment of the invention for enabling a subject to measure the accommodative state of his eye. As will be explained, the subject accomplishes this self-measurement by the act of subjectively noting the intersection of two scales visible to the subject in accordance with the further teaching of the present invention.

In the preferred embodiment of FIG. 1, the subject's eye 11 is shown looking into a pinhole aperture plate 13. The pinhole aperture plate 13 contains two pinhole apertures 15 and 17 located horizontally equidistant from the center 19 of the pinhole aperture plate 13. The distance between the centers (not shown) of the two pinhole apertures 15 and 17 is approximately 3 millimeters. It should, however, be realized that there can be more than two pinhole apertures in the pinhole aperture plate 13, and that they can be disposed in a vertical or horizontal alignment or in any other desired alignment near the center 19 of the pinhole aperture plate 13. Also, where there are more than two pinhole apertures in the plate 13, they can be aligned in any other suitable geometric configuration near or about the center 19.

A positive Badal lens 21 is placed in a position adjacent to the pinhole aperture plate 13 such that the optical axis 23 of the Badal lens 21 is coincident with the center 19 of the pinhole aperture plate 13. An exemplary 20 diopter Badal lens 21 is used in FIG. 1, giving a focal distance of 5 centimeters and an effective dioptric divergence (from the perspective of the subject's eye 11) of 4 diopters/centimeter away from the focal distance of the Badal lens 21.

The lower end 25 of an inclined scale 27 is placed adjacent to the lower edge 29 of the Badal lens 21. The scale 27 is inclined away from the Badal lens 21 so that the center 31 of the scale 27 is located on the optical axis 23 of the Badal lens 21 and at a distance of one focal length from the center 33 of the Badal lens 21. The upper end 35 of the inclined scale 27 is at a height above the optical axis 23 of the Badal lens 21 that is equal to the distance that the lower end 25 of the scale 27 is below the optical axis 23 of the Badal lens 21. The scale 27 has an exemplary length of slightly longer than 5 centimeters because it is corrected for the angle of incline relative to the optical axis 23 of the Badal lens 21.

In the preferred embodiment of FIG. 1, the scale 27 is comprised of a photographic negative with transparent major scale markings 37 and transparent minor or intermediate scale markings 39 to facilitate back lighting (to be explained). The center 31 of the scale 27, which is at one focal length from the center 33 of the Badal lens 21, is distinctively marked with a long horizontal line 41, which represents infinity. The distance between scale markings 37 and 39 is determined so that the major scale markings 37 represent a subject's dioptric deviation from infinity, or the long horizontal line 41, while the minor or intermediate scale markings 39 represent half diopter marks. Thus, the subject can readily perceive his state of accommodation by noting the number and type of markings between the long horizontal line 41 and the intersection of the two visible scales at that particular scale marking.

Actual scale marking distances may be calculated using the following relationship:

$$S_d = B^2 M - B$$

where $S_d$ is the subject's dioptric deviation in diopters, B is the power of the Badal lens 21 in diopters and M is the distance between the center 33 of the Badal lens 21 and the above-noted particular scale marking in meters. The distances so derived are for the optical axis 2 of the Badal lens 21 and must be trigonometrically expanded to account for the incline of said scale relative to said optical axis. Solving the equation gives the lens power required to correct a subject's eye 11 to infinity. That is, negative numbers indicate myopia, and positive numbers indicate hyperopia.

The preferred embodiment of FIG. 1 has a provision for the back-illumination of the scale 27 by using a light source 43, such as a light emitting diode, to illuminate a diffusing screen 45 which, in turn, illuminates the back side 47 of the scale 27. It is desirable that the light emitting diode 43 be of a narrow-bandwidth type emitting principally at about 585 nanometers wavelength (monochromatic yellow light) to minimize chromatic aberrations within the eye. A commercially available example of such a narrow-bandwidth light emitting diode is the HLMP 3850, manufactured by the Hewlett-Packard Corporation and by other manufacturers. While a light source 43 of monochromatic yellow light is preferred, it should be noted that a light source of any other wavelength or combination of wavelengths of visible light could be used for the back-illumination of the scale 27. The optometer apparatus shown in FIG. 1 may be contained within a tube (not shown) or other structure (not shown) and provided with a power source (P.S.) 48, such as a battery, to supply power to the light emitting diode 43. However, it should be realized that the power source 48 could also be an AC or DC power source or any other suitable power source.

As stated before, the long horizontal line 41 is at one focal length from the Badal lens 21. As a result, light ray bundles arriving from the horizontal line 41 and exiting from the apertures 15 and 17 will be collimated or parallel to each other. Light ray bundles that originate from the scale 27 at points or scale markings 37 and 39 closer to the Badal lens 21 than the horizontal line 41 will be diverging as they exit from the apertures 15 and 17. And finally, light ray bundles that originate from the scale 27 at points or scale markings 37 and 39 further away from the Badal lens 21 than the horizontal line 41 will be converging as they exit from the apertures 15 and 17. Thus, if the points or scale markings 37, 39 and 41 along the scale 27 are taken as a continuum of points along the length of the scale 27, it can be seen that the light ray bundles originating from these points and exiting from the apertures 15 and 17 will be first diverged, then collimated at one focal length and then converged, as the scale 27 is regarded from the point on the scale closest to the Badal lens 21 to the point on the scale 27 that is furtherest away from the Badal lens 21. The image-points (or light ray bundles originating from the scale markings 37, 39 and 41) exiting from the apertures 15 and 17 are also displaced vertically by the vertical orientation of the scale 27.

The lens in the subject's eye 11 may be emmetropic, myopic or hyperopic. In other words, the lens in the subject's eye 11 converges the entering light rays from an infinitely distant target exactly the right amount to be in focus on the retina (emmetropia), too much to be in focus on the retina (myopia) or not enough to be in focus on the retina (hyperopia).

FIGS. 2A, 2B and 2C respectively show the above-described three views of the image that may be seen by the eye of a user of the optometer apparatus of FIG. 1.

FIG. 2A indicates the emmetropic condition of the subject's eye 11, with the intersection of the two visible scales 49 and 51 coincident with the major horizontal line 41 indicating one focal length from the Badal lens 21. Such a scale reading indicates the desired state of accommodation at infinity.

FIG. 2B indicates the myopic condition of the subject's eye 11, where the intersection of the two visible scales 49 and 51 is coincident with the fifth major scale marking 37 below the major horizontal line 41 of the scale 27. Such a scale reading indicates 5 diopters of myopia.

FIG. 2C indicates the hyperopic condition where the intersection of the two visible scales 49 and 51 is coincident with three and a half major scale-markings (three major scale markings 37 and an additional minor scale marking 39) above the major horizontal line 41 of the scale 27. To the subject, this scale reading indicates 3½ diopters of hyperopia. The images shown in FIGS. 2A, 2B and 2C assume the orientation of the optometer apparatus shown in FIG. 1. That is, with the lower end 25 of the scale 27 closest to the subject being at the bottom of the optometer apparatus of FIG. 1 as the optometer apparatus is held by the subject.

When a subject's eye 11 views the optometer of FIG. 1 and is, for example, myopic, there is a specific point on the scale 27 (such as exemplary point 53 in FIG. 2B) that is closer to the Badal lens 21 than the horizontal line 41 and that emits light which exits from the apertures 15 and 17 as two bundles of light with the right amount of divergence to exactly cancel the excess convergence in the eye 11 that is myopic. As a result, the two bundles of light from the apertures 15 and 17 (and that originated from the specific point on the scale 27) are brought to coincidence on the retina of the subject's eye 11. All other points on the scale 27 will emit light bundles through the apertures 15 and 17 that either converge or diverge too much to be coincident on the retina of the subject's eye 11. Therefore, light from these other points on the scale 27 will paint a double image on the retina which, since they are vertically displaced as explained before, will appear to the subject's eye 11 as two scales that intersect at the point of coincidence, as shown in FIG. 2B.

A similar explanation can be made for the conditions of emmetropia and hyperopia, with the point of coincidence only being changed with the different conditions, as respectively indicated in FIGS. 2A and 2C.

The exit apertures 15 and 17 are small, thus causing the blur circles of images of points or markings on the scale 27 to also be small, and the scale 27 to appear to be in focus at a plurality of focal distances. Since the image being viewed by the subject's eye 11 appears to be in focus, there is no stimulus for accommodation. The lack of an accommodative stimulus effectively opens an accommodative control feedback loop, thus facilitating the attainment of cognitive control for the subject. Cognitive control is important in situations where there are no naturally occurring stimuli to accommodation, such as when flying in clouds or in the dark. A pilot would still want to maintain his focus at infinity under these conditions.

FIG. 3 shows actual data from one subject who was attempting to correct a condition of night myopia. All data points (1 through 15) are means and standard deviations of 20 readings, taken with a vernier optometer that did not provide feedback to the subject about his accommodative state. The first data point (0) on the left was a pre-screen condition and indicated approximately 2.8 diopters of night myopia. Subsequent data points (1 through 15) were taken following approximately 40 minute training sessions with examples of exemplary embodiments of the present invention. As can be seen from the data, this subject completely overcame his night myopia after 15 training sessions. Other subjects have shown similar results.

Therefore, what has been described is a Scheiner-principle optometer apparatus, and method therefor, for measuring the resting state of accommodation and for providing cognitive recognition of this accommodative state in order to facilitate bio-feedback training of that accommodative state. The optometer apparatus includes a pinhole aperture plate having a center and a plurality of apertures positioned in the pinhole aperture plate for viewing by the subject's eye, a positive lens disposed near the pinhole aperture plate and having an optical axis coincident with the center of the pinhole aperture plate, and scaled means inclined away from the positive lens for indicating to the subject the accommodative state of his eye in diopters.

As a subject uses the optometer apparatus of this invention, his eye 11 sees an "X" image with a scale that indicates where he is accommodating by the placement of the intersection of the "X" on the scale 27. The subject may directly read the scale 27 and either note or report this information as required, or he may attempt to manipulate his accommodation to achieve some desired end. The fundamental necessary condition of any bio-feedback training paradigm is to bring the physiological phenomenon of interest directly and concurrently into consciousness and the optometer apparatus of FIG. 1 does that.

It should therefore readily be understood that many modifications and variations of the present invention are possible within the purview of this invention. For example, the apertures may be two or more in number and they may be disposed in any desired orientation or position near or about the center of the pinhole aperture plate such as, for example, in a vertical or horizontal alignment or in any other desired alignment. In addition, the scale could even be positioned parallel to the optical axis of the Badal lens, as long as it was not on that optical axis. It is therefore to be understood that within the scope of the appended claims, the invention may be practiced otherwise than as specifically described.

What is claimed and desired to be secured by Letters Patent of the United States is:

1. An optometer apparatus for measuring the accommodative state of an eye of a subject, said optometer apparatus comprising:
   a pinhole aperture plate having a center and a plurality of apertures positioned in said pinhole aperture plate for viewing by the subject's eye;
   a positive lens disposed near said pinhole aperture plate and having an optical axis coincident with said center of said pinhole aperture plate; and
   scaled means inclined away from said positive lens for indicating to the subject the accommodative state of the subject's eye in diopters.

2. The optometer apparatus of claim 1 wherein said plurality of apertures includes:
   first and second apertures positioned on opposite sides of said center of said pinhole aperture plate.

3. The optometer apparatus of claim 1 wherein:
   said positive lens is a positive Badal lens.

4. The optometer apparatus of claim 1 wherein:
said plurality of apertures are Scheiner apertures.

5. The optometer apparatus of claim 1 wherein:
said scaled means includes a scale having a center marking located on said optical axis of said positive lens at a distance of substantially one focal length from said positive lens and having markings on opposite sides of said center marking at different focal distances from said positive lens to enable the subject to determine his dioptric deviation from the center marking as a function of the number of markings from the center marking to the intersection of a plurality of scales visible to the subject.

6. The optometer apparatus of claim 5 wherein said scale is comprised of transparent markings and said optometer apparatus further includes:
means for backlighting said scale.

7. The optometer apparatus of claim 6 wherein said backlighting means includes:
a light source for emitting light to backlight said scale; and
a power source for supplying power to said light source.

8. The optometer apparatus of claim 7 wherein:
said light source is a monochromatic light source for emitting light at a preselected wavelength.

9. The optometer apparatus of claim 7 wherein:
said positive lens is a positive Badal lens.

10. An optometer apparatus for measuring the accommodative state of an eye of a subject, said optometer apparatus comprising:
a pinhole aperture plate having a center and a plurality of apertures disposed in said pinhole aperture plate for viewing by the subject's eye;
a positive Badal lens disposed near said pinhole aperture plate and having an optical axis coincident with said center of said pinhole aperture plate; and
an inclined scale having a center marking located on said optical axis of said positive Badal lens at a distance of substantially one focal length from said positive lens and having markings on opposite sides of said center marking at different focal distances from said positive Badal lens to indicate to the subject the accommodative state of the subject's eye in diopters.

11. The optometer apparatus of claim 10 wherein said plurality of apertures includes:
first and second horizontally positioned apertures disposed on opposite sides of said center of said pinhole aperture plate.

12. A method for enabling a subject to measure the accommodative state of his own eye, said method comprising the steps of:
providing first and second apertures positioned on opposite sides of an optical axis for viewing by the subject's eye;
providing a scaled target;
projecting an image of the scaled target through the first and second aperture as first and second rays of light to form an "X" image with a scale;
indicating to the subject the accommodative state of his eye by the position of the intersection of the "X" image on the scale.

13. The method of claim 12 wherein said providing step includes the step of:
utilizing two pinhole apertures positioned on opposing sides of the optical axis of a pinhole aperture plate as the first and second apertures.

14. The method of claim 12 wherein said projecting step includes the step of:
emitting monochromatic light from a monochromatic light source; and
utilizing a positive Badal lens to focus the monochromatic image of the scaled target through the first and second apertures.

* * * * *